US012564543B2

(12) United States Patent
Matsuura et al.

(10) Patent No.: US 12,564,543 B2
(45) Date of Patent: Mar. 3, 2026

(54) DENTAL COMPOSITION

(71) Applicant: KURARAY NORITAKE DENTAL INC., Kurashiki (JP)

(72) Inventors: Ryo Matsuura, Niigata (JP); Tatsuya Kajikawa, Niigata (JP)

(73) Assignee: KURARAY NORITAKE DENTAL INC., Kurashiki (JP)

( * ) Notice: Subject to any disclaimer, the term of this patent is extended or adjusted under 35 U.S.C. 154(b) by 933 days.

(21) Appl. No.: 17/766,827

(22) PCT Filed: Oct. 7, 2020

(86) PCT No.: PCT/JP2020/038035

§ 371 (c)(1),
(2) Date: Apr. 6, 2022

(87) PCT Pub. No.: WO2021/070875

PCT Pub. Date: Apr. 15, 2021

(65) Prior Publication Data

US 2023/0390163 A1 Dec. 7, 2023

(30) Foreign Application Priority Data

Oct. 8, 2019 (JP) ................................ 2019-185497

(51) Int. Cl.

| | |
|---|---|
| ***A61K 6/887*** | (2020.01) |
| ***A61K 6/30*** | (2020.01) |
| ***A61K 6/62*** | (2020.01) |
| ***C08L 33/08*** | (2006.01) |
| ***C08L 33/10*** | (2006.01) |

(52) U.S. Cl.

CPC ................ *A61K 6/887* (2020.01); *A61K 6/30* (2020.01); *A61K 6/62* (2020.01); *C08L 33/08* (2013.01); *C08L 33/10* (2013.01)

(58) Field of Classification Search

CPC ........... A61K 6/887; A61K 6/62; C08L 33/08; C08L 33/10

See application file for complete search history.

(56) References Cited

U.S. PATENT DOCUMENTS

| | | | |
|---|---|---|---|
| 4,719,297 | A | 1/1988 | Henne et al. |
| 2003/0175660 | A1 | 9/2003 | Yin et al. |
| 2004/0110864 | A1 | 6/2004 | Hecht et al. |
| 2010/0036075 | A1 | 2/2010 | Ishino et al. |
| 2010/0130682 | A1 | 5/2010 | Hinamoto et al. |
| 2015/0257985 | A1 | 9/2015 | Sadowsky et al. |

FOREIGN PATENT DOCUMENTS

| | | | | |
|---|---|---|---|---|
| EP | 0438628 | A2 | | 7/1991 |
| EP | 2153811 | A2 | | 2/2010 |
| GB | 1465897 | A | | 3/1977 |
| JP | S50-42696 | A | | 4/1975 |
| JP | S57-197289 | A | | 12/1982 |
| JP | H09-3109 | A | | 1/1997 |
| JP | H10-245525 | A | | 9/1998 |
| JP | 2004529946 | A | | 9/2004 |
| JP | 2005053898 | A | * | 3/2005 |
| JP | 2006510583 | A | | 3/2006 |
| JP | 2007217447 | A | | 8/2007 |
| JP | 2008260752 | A | | 10/2008 |
| JP | 2009184971 | A | | 8/2009 |
| JP | 2011144121 | A | | 7/2011 |
| JP | 2012171885 | A | | 9/2012 |
| WO | WO-2004017928 | | | 3/2004 |
| WO | WO-2008087977 | A1 | | 7/2008 |
| WO | WO-2014095724 | A1 | | 6/2014 |

OTHER PUBLICATIONS

Machine translation of JP-2005053898-A obtained from PE2E Search (Year: 2005).*

Extended European Search Report issued Sep. 18, 2023 in Patent Application No. 20874394.8, 11 pages.

International Search Report issued Dec. 8, 2020 in PCT/JP2020/038035 (with English translation), 4 pages.

* cited by examiner

*Primary Examiner* — Kregg T Brooks

*Assistant Examiner* — David R. Foss

(74) *Attorney, Agent, or Firm* — Element IP, PLC

(57) ABSTRACT

An object of the present invention is to provide a dental composition that shows desirable adhesive properties to tooth structure, and that has desirable mechanical strength in the form of a cured product while having low polymerization shrinkage stress. The present invention relates to a dental composition comprising: a (meth)acrylic compound (A); a monomer (B) having an acidic group and a molecular weight of less than 5,000; a monomer (C) having no acidic group and having a molecular weight of less than 5,000; and a polymerization initiator (D), the (meth)acrylic compound (A) having an average molecular weight of 5,000 to 50,000, and an average molecular weight of 1,250 or more and less than 20,000 per (meth)acryl group.

16 Claims, No Drawings

DENTAL COMPOSITION

TECHNICAL FIELD

The present invention relates to dental compositions used in the field of dentistry.

BACKGROUND ART

Dental restorations using dental bonding materials and dental composite resins are a common form of treatment of tooth decay and associated defects. A restorative dental treatment using these materials follows the following procedure. First, the decayed area is drilled away to create space, and a dental bonding material is applied to the drilled hole. The dental bonding material in the damaged area is then irradiated with visible light to cure. After cure, a dental composite resin is filled over the cured layer of dental bonding material, and is cured by applying visible light.

Instead of using a dental bonding material and a dental composite resin as in this restorative technique using these two materials, a newer technique uses a dental composite resin that has been developed to possess adhesive properties, and such self-adhesive dental composite resins have been used in actual practice to enable a simpler restorative treatment procedure that can skip the use of dental bonding material.

A self-adhesive dental composite resin contains a polyfunctional monomer and a filler, which are added with the primary purpose of imparting high mechanical strength to the cured product, and a polymerization initiator, the main purpose of which is to improve curability. In addition to these components of a traditional dental composite resin, a self-adhesive dental composite resin also contains a monomer having an acidic group—a common component used in traditional dental bonding materials to have adhesive properties to tooth structure (see, for example, Patent Literatures 1 and 2).

Polyfunctional (meth)acrylates are compounds commonly used as such polyfunctional monomers. For example, it is stated in Patent Literature 1 that compounds such as 2,2-bis(4-(meth)acryloyloxypolyethoxyphenyl)propane, and polyethylene glycol di(meth)acrylate may be used in addition to polyfunctional monomers having a backbone that is primarily sugar alcohol and the like. In Patent Literature 2, it is stated that a monomer having at least two ethylenic unsaturated groups can be used (for example, polyethylene glycol di(meth)acrylate, polypropylene glycol di(meth)acrylate). Typically, polyfunctional monomers having relatively small molecular weights are used to increase the density of polymerizable groups and impart high mechanical strength. In Patent Literature 2, the molecular weight of the monomer having at least two ethylenic unsaturated groups ranges from 270 to 900. Patent Literature 1 mentions 2,2-bis(4-(meth)acryloyloxypolyethoxyphenyl)propane as a polyfunctional monomer that is particularly suited when the average degree of polymerization of oxyethylene chain is 1 to 4. The 2,2-bis(4-methacryloyloxypolyethoxyphenyl)propane used in Example of this patent document has, on average, 2.6 oxyethylene chains per molecule.

A composition, for example, a dental composite resin, containing a monomer such as a (meth)acrylic monomer is known to typically decrease its volume as a result of polymerization shrinkage that occurs during polymerization and cure. In conventional restorative dental treatments using dental bonding materials and dental composite resins, the stress due to volume shrinkage that occurs during polymerization and cure of a dental composite resin (hereinafter, also referred to as "polymerization shrinkage stress") concentrates at the bonding interface between the tooth structure and the dental bonding material. While such polymerization shrinkage stress is a potential cause of marginal leakage and loose restorations, the recent advances in the performance of dental bonding material have helped reduce such problems in clinical practice.

However, the compositions described in Patent Literatures 1 and 2 can become a problem when these are directly applied to tooth structure as self-adhesive dental composite resins without using a dental bonding material because, while these compositions have desirable adhesive properties to tooth structure and provide desirable mechanical strength, the related art does not take into consideration polymerization shrinkage stress. In fact, studies by the present inventors found that there is still room for improvement concerning polymerization shrinkage stress.

With regard to polymerization shrinkage stress, a self-adhesive dental composite resin is proposed that uses, for example, a long-chain polyfunctional monomer of a specific structure in specified amounts to reduce polymerization shrinkage stress, and to provide high adhesive properties to tooth structure, high mechanical strength, and low polymerization shrinkage stress (Patent Literature 3). However, after examinations by the present inventors, it was found that the self-adhesive dental composite resin proposed in Patent Literature 3, despite having reduced polymerization shrinkage stress compared to the related art available at the time of the filing of this patent document, needs further improvements in terms of polymerization shrinkage stress, particularly when considering the potential risk of, for example, detachment or marginal leakage in cases where polymerization shrinkage stress has a large effect, for example, such as in relatively deep cavities.

Dental compositions containing an oligomer are known (for example, Patent Literatures 4 to 7). However, in Patent Literatures 4 to 6, the idea of adding an oligomer is directed to improving mechanical strength, not to reduce polymerization shrinkage stress. In fact, addition of an oligomer did not reduce polymerization shrinkage stress as desired in investigations conducted by the present inventors.

Patent Literature 7 describes a dental restorative filling kit containing a specified amount of an unsaturated urethane-based oligomer having a weight-average molecular weight of 1,000 to 50,000. However, the dental restorative filling kit does not contain an acidic monomer, and there is no adhesive properties to tooth structure. The desired effect of reducing polymerization shrinkage stress was also found to be absent by investigations conducted by the present inventors.

CITATION LIST

Patent Literature

Patent Literature 1: JP 2008-260752 A

Patent Literature 2: Publication of European Patent Application, No. 2153811

Patent Literature 3: JP 2012-171885 A

Patent Literature 4: JP 50(1975)-042696 A

Patent Literature 5: JP 2006-510583 T

Patent Literature 6: JP 2009-184971 A

Patent Literature 7: JP 2011-144121 A

SUMMARY OF INVENTION

Technical Problem

As discussed above, no self-adhesive dental composite resin is available that excels in adhesive properties to tooth structure, mechanical strength, and polymerization shrinkage stress at the same time.

It is accordingly an object of the present invention to provide a dental composition that shows desirable adhesive properties to tooth structure, and that has desirable mechanical strength in the form of a cured product while having low polymerization shrinkage stress.

Solution to Problem

The present inventors conducted intensive studies, and found that the foregoing issues can be solved with specific (meth)acrylic compounds. The present invention was completed after further studies.

Specifically, the present invention includes the following.

[1] A dental composition comprising: a (meth)acrylic compound (A) having a weight-average molecular weight of 5,000 to 50,000; a monomer (B) having an acidic group and a molecular weight of less than 5,000; a monomer (C) having no acidic group and having a molecular weight of less than 5,000; and a polymerization initiator (D), the (meth)acrylic compound (A) having a weight-average molecular weight of 1,250 or more and less than 20,000 per (meth)acryl group.

[2] The dental composition according to [1], wherein the (meth)acrylic compound (A) is a urethanized (meth)acrylic compound (A-1).

[3] The dental composition according to [1] or [2], wherein the content of the (meth)acrylic compound (A) is 0.1 to 30 parts by mass in total 100 parts by mass of the (meth)acrylic compound (A), the monomer (B) having an acidic group, and the monomer (C) having no acidic group.

[4] The dental composition according to any one of [1] to [3], wherein the (meth)acrylic compound (A) has a viscosity at 25° C. of 5,000 cps or more.

[5] The dental composition according to any one of [1] to [4], wherein the (meth)acrylic compound (A) has a glass transition temperature (Tg) of 20° C. or less.

[6] The dental composition according to any one of [1] to [5], wherein the (meth)acrylic compound (A) has a weight-average molecular weight of 6,100 or more and less than per (meth)acryl group.

[7] The dental composition according to any one of [2] to [6], wherein the urethanized (meth)acrylic compound (A-1) is a (meth)acrylate having: a structure selected from the group consisting of a polyester, a polycarbonate, a polyurethane, a polyether, a poly-conjugated diene, and a hydrogenated poly-conjugated diene; and a urethane bond.

[8] The dental composition according to any one of [1] to [7], wherein the monomer (B) having an acidic group and a molecular weight of less than 5,000 comprises a phosphoric acid group-containing monomer.

[9] The dental composition according to any one of [1] to [8], wherein the monomer (C) having no acidic group and having a molecular weight of less than 5,000 comprises a hydrophobic monomer (C-1) having no acidic group and having a molecular weight of less than 5,000.

[10] The dental composition according to [9], wherein the hydrophobic monomer (C-1) having no acidic group and having a molecular weight of less than 5,000 comprises an aliphatic compound-based bifunctional monomer.

[11] The dental composition according to any one of [1] to [10], wherein the polymerization initiator (D) comprises: a water-soluble photopolymerization initiator (D-1) having a solubility at 25° C. of 10 g/L or more in water; and a water-insoluble photopolymerization initiator (D-2) having a solubility at 25° C. of less than 10 g/L in water.

[12] A self-adhesive dental composite resin comprising a dental composition of any one of [1] to [11].

[13] A dental bonding material comprising a dental composition of any one of [1] to [11].

[14] A dental cement comprising a dental composition of any one of [1] to [11].

Advantageous Effects of Invention

According to the present invention, a dental composition is provided that shows desirable adhesive properties to tooth structure, and that has desirable mechanical strength in the form of a cured product while having low polymerization shrinkage stress. With these features, the dental composition can be suitably used in applications such as self-adhesive dental composite resins, dental bonding materials, and dental cements. Specifically, the present invention can provide a self-adhesive dental composite resin, a dental bonding material, or a dental cement with which the potential risk of, for example, detachment or marginal leakage can be reduced even in cases where polymerization shrinkage stress has a large effect, for example, such as in relatively deep cavities.

DESCRIPTION OF EMBODIMENTS

A dental composition of the present invention comprises, as essential components, a (meth)acrylic compound (A) having a weight-average molecular weight of 5,000 to 50,000; a monomer (B) having an acidic group and a molecular weight of less than 5,000; a monomer (C) having no acidic group and having a molecular weight of less than 5,000; and a polymerization initiator (D), the (meth)acrylic compound (A) having a weight-average molecular weight of 1,250 or more and less than 20,000 per (meth)acryl group. The term "(meth)acryl" as used in the present specification collectively refers to methacryl and acryl. The same applies to similar expressions. In the present specification, the upper limits and lower limits of numeric ranges (for example, ranges of contents of components, ranges of values calculated from components, and numeric ranges of physical properties) can be combined appropriately.

It remains somewhat unclear why a dental composition of the present invention shows desirable adhesive properties to tooth structure and has desirable mechanical strength in the form of a cured product while having low polymerization shrinkage stress. However, a possible explanation is that the (meth)acrylic compound (A) contained in the dental composition relieves the stress that results from polymerization shrinkage. While a low-molecular-weight monomer alone provides very high curability, such monomers have a high crosslink density, and increases the polymerization shrinkage rate. This inevitably increases the shrinkage stress that occurs during polymerization. The (meth)acrylic compound (A) used in the present invention has a relatively large molecular weight, and the ratio of its molecular weight to the polymerizable group is confined in a specific range. The resulting moderate decrease in the crosslink density of the polymer matrix is probably responsible for the notable relaxation of the stress exerted during polymerization, and the maintained mechanical strength. This should explain the high adhesion exhibited by a dental composition of the present invention even in conditions simulating cases where polymerization shrinkage stress has a large effect, for example, such as in the restorative treatment of relatively deep cavities.

The following describes the components used in a dental composition of the present invention.

(Meth)Acrylic Compound (A) Having a Weight-Average Molecular Weight of 5,000 to 50,000

The (meth)acrylic compound (A) having a weight-average molecular weight of 5,000 to 50,000 (hereinafter, referred to as "(meth)acrylic compound (A)") used in a dental composition of the present invention is used to impart low polymerization shrinkage stress and high bond strength.

The (meth)acrylic compound (A) can be broadly classified into a urethanized (meth)acrylic compound (A-1), and a (meth)acrylic compound having no urethane bond. In view of the ease of introducing a (meth)acryl group and the effect to reduce polymerization shrinkage stress, the (meth)acrylic compound (A) is preferably a urethanized (meth)acrylic compound (A-1). The urethanized (meth)acrylic compound (A-1) can be synthesized with ease by, for example, an addition reaction of a polyol containing a polymer backbone (described later), a compound having an isocyanate group (—NCO), and a (meth)acrylic compound having a hydroxyl group (—OH). Alternatively, the urethanized (meth)acrylic compound (A-1) can be easily synthesized by allowing lactone or alkylene oxide to undergo a ring-opening addition reaction with a (meth)acrylic compound having a hydroxyl group, and causing the resulting compound having a terminal hydroxyl group to undergo an addition reaction with a compound having an isocyanate group. The (meth)acrylic compound that donates a (meth)acryl group to a polymer can introduce a (meth)acryl group by, for example, a dehydrocondensation reaction of (meth)acrylic acid with a polymer of a monomer having a hydroxyl group. The (meth)acrylic compound (A) may be used alone, or two or more thereof may be used in combination.

Urethanized (Meth)Acrylic Compound (A-1)

The urethanized (meth)acrylic compound (A-1) is preferably a (meth)acrylate having a structure (polymer backbone) selected from the group consisting of a polyester, a polycarbonate, a polyurethane, a polyether, a poly-conjugated diene, and a hydrogenated poly-conjugated diene, in addition to a urethane bond. More preferably, the urethanized (meth)acrylic compound (A-1) is a (meth)acrylate having, within the molecule, a urethane bond, and at least one polyol moiety selected from the group consisting of a polyester, a polycarbonate, a polyurethane, a polyether, a poly-conjugated diene, and a hydrogenated poly-conjugated diene each having a structure derived from a C4 to C18 aliphatic diol unit having a branched structure. The polyester, polycarbonate, polyurethane, polyether, poly-conjugated diene, and hydrogenated poly-conjugated diene are not particularly limited, as long as these have the above structure.

Examples of the polyester include: a polymer of a dicarboxylic acid (e.g., an aromatic dicarboxylic acid such as phthalic acid or isophthalic acid, or an unsaturated aliphatic dicarboxylic acid such as maleic acid) and an aliphatic diol having 2 to 18 carbon atoms; a polymer of a dicarboxylic acid (e.g., a saturated aliphatic dicarboxylic acid such as adipic acid or sebacic acid) and an aliphatic diol having 2 to 18 carbon atoms; a polymer of β-propiolactone; a polymer of γ-butyrolactone; a polymer of δ-valerolactone; a polymer of ε-caprolactone; and a copolymer of these. Preferred are a polymer of a dicarboxylic acid (an aromatic dicarboxylic acid such as phthalic acid or isophthalic acid, or an unsaturated aliphatic dicarboxylic acid such as maleic acid) and an aliphatic diol having 2 to 12 carbon atoms; and a polymer of a dicarboxylic acid (a saturated aliphatic dicarboxylic acid such as adipic acid or sebacic acid) and an aliphatic diol having 2 to 12 carbon atoms.

Examples of the polycarbonate include a polycarbonate derived from an aliphatic diol having 2 to 18 carbon atoms, a polycarbonate derived from bisphenol A, and a polycarbonate derived from a C2 to C18 aliphatic diol and bisphenol A. Preferred are a polycarbonate derived from an aliphatic diol having 2 to 12 carbon atoms, a polycarbonate derived from bisphenol A, and a polycarbonate derived from a C2 to C12 aliphatic diol and bisphenol A.

Examples of the polyurethane include a polymer of a C2 to C18 aliphatic diol and a C1 to C18 diisocyanate. Preferred is a polymer of a C2 to C12 aliphatic diol and a C1 to C12 diisocyanate.

Examples of the polyether include polyethylene glycol, polypropylene glycol, polybutylene glycol, and poly(1-methylbutylene glycol).

Examples of the poly-conjugated diene and hydrogenated poly-conjugated diene include 1,4-polybutadiene, 1,2-polybutadiene, polyisoprene, poly(butadiene-isoprene), poly(butadiene-styrene), poly(isoprene-styrene), polyfarnesene, and hydrogenated products of these.

Among these structures, a polyester, a polycarbonate, and a poly-conjugated diene are preferred in view of desirable mechanical strength and water resistance. A polyol having the polymer backbone mentioned above can be used for the production of urethanized (meth)acrylic compound (A-1).

Examples of the compound having an isocyanate group include hexamethylene diisocyanate (HDI), tolylene diisocyanate (TDI), xylylene diisocyanate (XDI), diphenylmethane diisocyanate (MDI), isophorone diisocyanate (IPDI), trimethylhexamethylene diisocyanate (TMHMDI), tricyclodecane diisocyanate (TCDDI), and adamantane diisocyanate (ADI).

Examples of the (meth)acrylic compound having a hydroxyl group include:

- hydroxy (meth)acrylate compounds, for example, such as 2-hydroxyethyl (meth)acrylate, 2-hydroxypropyl (meth)acrylate, 2-hydroxybutyl (meth)acrylate, 6-hydroxyhexyl (meth)acrylate, 10-hydroxydecyl (meth) acrylate, 3-chloro-2-hydroxypropyl (meth)acrylate, 2-hydroxy-3-phenoxypropyl (meth)acrylate, glycerin mono(meth)acrylate, 2-hydroxy-3-acryloyloxypropyl (meth)acrylate, 2,2-bis[4-[3-(meth)acryloyloxy-2-hydroxypropoxy]phenyl]propane, 1,2-bis[3-(meth)acryloyloxy-2-hydroxypropoxy]ethane, pentaerythritol tri (meth)acrylate, and tri or tetra(meth)acrylates of dipentaerythritol; and
- hydroxy (meth)acrylamide compounds, for example, such as N-hydroxyethyl (meth)acrylamide, and N,N-bis(2-hydroxyethyl)(meth)acrylamide.

Examples of the C4 to C18 aliphatic diol having a branched structure include 2-methyl-1,3-propanediol, 2,2-diethyl-1,3-propanediol, 1,3-butanediol, 2-methyl-1,4-butanediol, neopentyl glycol, 3-methyl-1,5-pentanediol, 2-methyl-1,8-octanediol, 2,7-dimethyl-1,8-octanediol, 2-methyl-1,9-nonanediol, 2,8-dimethyl-1,9-nonanediol, 2-methyl-1,10-decanediol, 2,9-dimethyl-1,10-decanediol, 2-methyl-1,11-undecanediol, 2,10-dimethyl-1,11-undecanediol, 2-methyl-1,12-dodecanediol, 2,11-dimethyl-1,12-dodecanediol, 2-methyl-1,13-tridecanediol, 2,12-dimethyl-1,13-tridecanediol, 2-methyl-1,14-tetradecanediol, 2,13-dimethyl-1,14-tetradecanediol, 2-methyl-1,15-pentadecanediol, 2,14-dimethyl-1,15-pentadecanediol, 2-methyl-1,16-hexadecanediol, and 2,15-dimethyl-1,16-hexadecanediol. In view of providing a dental composition having desirable curability, the polyol components used are preferably C5 to C12 aliphatic diols having a methyl-group side chain, for example, such as 2-methyl-1,4-butanediol, 3-methyl-1,5-pentanediol, 2-methyl-1,8-octanediol, 2,7-dimethyl-1,8-octanediol, 2-methyl-1,9-nonanediol, and 2,8-dimethyl-1,9-nonanediol. The polyol components are more preferably 2-methyl-1,4-butanediol, 3-methyl-1,5-pentanediol, 2-methyl-1,8-octanediol, and 2,7-dimethyl-1,8-octanediol, even more preferably 3-methyl-1,5-pentanediol, and 2-methyl-1,8-octanediol.

The addition reaction of the compound having an isocyanate group and the (meth)acrylic compound having a hydroxyl group can be performed following a known method, and the method is not particularly limited.

The urethanized (meth)acrylic compound (A-1) produced is, for example, a product of a reaction of any combination of: a polyol having at least one structure selected from the group consisting of a polyester, a polycarbonate, a polyurethane, a polyether, a poly-conjugated diene, and a hydrogenated poly-conjugated diene; a compound having an isocyanate group; and a (meth)acrylic compound having a hydroxyl group.

In view of viscosity and reduction of polymerization shrinkage stress, the (meth)acrylic compound (A) has a weight-average molecular weight (Mw) of 5,000 to 50,000, preferably 6,000 to 30,000, more preferably 7,500 to 20,000. In certain embodiments of the present invention, the (meth)acrylic compound (A) has a weight-average molecular weight (Mw) of preferably 12,100 to 50,000, more preferably 12,500 to 30,000, even more preferably 12,500 to 20,000. As used herein, "weight-average molecular weight (Mw)" means a weight-average molecular weight in terms of polystyrene as determined by gel permeation chromatography (GPC).

The crosslink density increases, and polymerization shrinkage stress cannot be reduced sufficiently when the number of (meth)acryl groups representing polymerizable groups of (meth)acrylic compound (A) is excessively large. On the other hand, the crosslink density and thus mechanical strength decrease when the number of (meth)acryl groups is too small. In this respect, the weight-average molecular weight of (meth)acrylic compound (A) per (meth)acryl group is 1,250 or more and less than 20,000, preferably 1,500 to 17,500, more preferably 1,800 to 16,000, even more preferably 2,500 to 15,000. In certain embodiments of the present invention, the weight-average molecular weight of (meth)acrylic compound (A) per (meth)acryl group is 6,100 or more and less than 20,000, preferably 6,200 to 17,500, more preferably 6,250 to 16,000, even more preferably 6,500 to 15,000. When the (meth)acrylic compound (A) is containing polymerizable groups other than (meth)acryl groups, for example, such as vinyl groups and styrene groups, it is preferable that the (meth)acrylic compound (A) contain preferably at most 2, more preferably zero polymerizable group other than (meth)acryl groups because the presence of such polymerizable groups may lead to increased polymerization shrinkage stress depending on the form of polymerization.

In view of reducing polymerization shrinkage stress, the (meth)acrylic compound (A) has a glass transition temperature (Tg) of preferably −100° C. to 20° C., more preferably −75° C. to 15° C., even more preferably −60° C. to 10° C. The glass transition temperature (Tg) of (meth)acrylic compound (A) can be measured using a known method with a device such as a viscoelasticity meter (rheometer) or a differential scanning calorimeter (DSC). For example, the glass transition temperature (Tg) can be measured by measuring the dynamic viscoelasticity of (meth)acrylic compound (A) with a rotary rheometer (AR 2000 manufactured by TA Instruments Japan Inc.), and finding the temperature at which tan δ shows a peak in the dynamic viscoelasticity measurement performed at 10 Hz frequency under a 10 N load with 0.1% displacement and 20 μNm torque.

In view of ease of handling and reduction of polymerization shrinkage stress, the (meth)acrylic compound (A) has a viscosity at 25° C. of preferably 5,000 to 10,000,000 cps, more preferably 10,000 to 7,500,000 cps, even more preferably 20,000 to 7,000,000 cps. In the present invention, "viscosity" means a viscosity measured at 25° C. with a Brookfield viscometer. Measurement conditions such as time and rotational speed are appropriately adjusted according to the viscosity range.

The (meth)acrylic compound (A) may be a commercially available product. Examples of such commercially available products include the Art Resin Series manufactured by Negami Chemical Industrial Co., Ltd., including, for example, UN-350, UN-353, UN-7700, UN-1255 (viscosity: >2,000,000 cps/25° C., weight-average molecular weight (Mw): 8,000, glass transition temperature (Tg): −14° C.; number of acryl groups: 2), UN-6200 (viscosity: 15,000 to 40,000 cps, weight-average molecular weight (Mw): 6,500, glass transition temperature (Tg): −52° C., polyether backbone, number of acryl groups: 2), UN-6202 (viscosity: 7,000 to 23,000 cps/25° C., weight-average molecular weight (Mw): 11,000, glass transition temperature (Tg): −41° C., polyether backbone, number of acryl groups: 2), UN-6204 (viscosity: >200,000 cps/25° C., weight-average molecular weight (Mw): 13,000, glass transition temperature (Tg): −74° C., polyether backbone, number of acryl groups: 2), UN-6205 (viscosity: >1,600,000 cps/25° C., weight-average molecular weight (Mw): 27,000, glass transition temperature (Tg): −74° C., polyether backbone, number of acryl groups: 2), UN-9000PEP (viscosity: >2,000,000 cps/25° C., weight-average molecular weight (Mw): 5,000, glass transition temperature (Tg): −7° C., polycarbonate backbone, number of acryl groups: 2), and UN-9000A (viscosity: >2,000,000 cps/25° C., weight-average molecular weight (Mw): 15,000, glass transition temperature (Tg): −27° C., polycarbonate backbone, number of acryl groups: 2).

In view of mechanical strength, paste properties, and reduction of polymerization shrinkage stress, the content of (meth)acrylic compound (A) in a dental composition of the present invention is preferably 0.1 to 30 parts by mass, more preferably 0.5 to 25 parts by mass, even more preferably 1 to 20 parts by mass relative to total 100 parts by mass of the (meth)acrylic compound (A), the monomer (B) having an acidic group and a molecular weight of less than 5,000, and the monomer (C) having no acidic group and having a molecular weight of less than 5,000.

Monomer (B) Having an Acidic Group and a Molecular Weight of Less than 5,000

The monomer (B) having an acidic group and a molecular weight of less than 5000 (hereinafter, referred to as "monomer (B) having an acidic group") has acid etching effect and priming effect, and is a component that provides demineralizing effect and penetrative effect. The monomer (B) having an acidic group is also polymerizable, and provides curing effect. The adhesive properties to tooth structure, and bond durability improve by containing the monomer (B) having an acidic group.

The monomer (B) having an acidic group is, for example, a monomer having at least one acidic group (such as a phosphoric acid group, a pyrophosphoric acid group, a thiophosphoric acid group, a phosphonic acid group, a sulfonic acid group, and a carboxylic acid group), and at least one polymerizable group (such as a (meth)acryloyl group, a vinyl group, and a styrene group). In view of adhesive properties to tooth structure, the monomer (B) having an acidic group is preferably a phosphoric acid group-containing monomer. Specific examples of the monomer (B) having an acidic group are as follows.

Examples of the phosphoric acid group-containing monomer include phosphoric acid group-containing (meth)acrylic monomers, for example, such as 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts of these.

Examples of the pyrophosphoric acid group-containing monomer include pyrophosphoric acid group-containing (meth)acrylic monomers, for example, such as bis[2-(meth)acryloyloxyethyl]pyrophosphate, bis[4-(meth)acryloyloxybutyl]pyrophosphate, bis[6-(meth)acryloyloxyhexyl]pyrophosphate, bis[8-(meth)acryloyloxyoctyl]pyrophosphate, bis[10-(meth)acryloyloxydecyl]pyrophosphate, and acid chlorides, alkali metal salts, and ammonium salts of these.

Examples of the thiophosphoric acid group-containing monomer include 2-(meth)acryloyloxyethyl dihydrogen thiophosphate, 3-(meth)acryloyloxypropyl dihydrogen thiophosphate, 4-(meth)acryloyloxybutyl dihydrogen thiophosphate, 5-(meth)acryloyloxypentyl dihydrogen thiophosphate, 6-(meth)acryloyloxyhexyl dihydrogen thiophosphate, 7-(meth)acryloyloxyheptyl dihydrogen thiophosphate, 8-(meth)acryloyloxyoctyl dihydrogen thiophosphate, 9-(meth)acryloyloxynonyl dihydrogen thiophosphate, 10-(meth)acryloyloxydecyl dihydrogen thiophosphate, 11-(meth)acryloyloxyundecyl dihydrogen thiophosphate, 12-(meth)acryloyloxydodecyl dihydrogen thiophosphate, 16-(meth)acryloyloxyhexadecyl dihydrogen thiophosphate, 20-(meth)acryloyloxyicosyl dihydrogen thiophosphate, and acid chlorides, alkali metal salts, and ammonium salts of these.

Examples of the phosphonic acid group-containing monomer include 2-(meth)acryloyloxyethylphenylphosphonate, 5-(meth)acryloyloxypentyl-3-phosphonopropionate, 6-(meth)acryloyloxyhexyl-3-phosphonopropionate, 10-(meth)acryloyloxydecyl-3-phosphonopropionate, 6-(meth)acryloyloxyhexyl-3-phosphonoacetate, 10-(meth)acryloyloxydecyl-3-phosphonoacetate, and acid chlorides, alkali metal salts, and ammonium salts of these.

Examples of the sulfonic acid group-containing monomer include 2-(meth)acrylamide-2-methylpropanesulfonic acid, styrenesulfonic acid, and 2-sulfoethyl(meth)acrylate.

Examples of the carboxylic acid group-containing monomer include monomers having one carboxy group within the molecule, and monomers having a plurality of carboxy groups within the molecule.

Examples of monomers having one carboxy group within the molecule include (meth)acrylic acid, N-(meth)acryloylglycine, N-(meth)acryloylaspartic acid, O-(meth)acryloyltyrosine, N-(meth)acryloyltyrosine, N-(meth)acryloylphenylalanine, N-(meth)acryloyl-p-aminobenzoic acid, N-(meth)acryloyl-o-aminobenzoic acid, p-vinyl benzoic acid, 2-(meth)acryloyloxybenzoic acid, 3-(meth)acryloyloxybenzoic acid, 4-(meth)acryloyloxybenzoic acid, N-(meth)acryloyl-5-aminosalicylic acid, N-(meth)acryloyl-4-aminosalicylic acid, 2-(meth)acryloyloxyethyl hydrogen succinate, 2-(meth)acryloyloxyethyl hydrogen phthalate, 2-(meth)acryloyloxyethyl hydrogen malate, and acid halides of these.

Examples of monomers having a plurality of carboxy groups within the molecule include 6-(meth)acryloyloxyhexane-1,1-dicarboxylic acid, 9-(meth)acryloyloxynonane-1,1-dicarboxylic acid, 10-(meth)acryloyloxydecane-1,1-dicarboxylic acid, 11-(meth)acryloyloxyundecane-1,1-dicarboxylic acid, 12-(meth)acryloyloxydodecane-1,1-dicarboxylic acid, 13-(meth)acryloyloxytridecane-1,1-dicarboxylic acid, 4-(meth)acryloyloxyethyltrimellitate, 4-(meth)acryloyloxyethyltrimellitate anhydride, 4-(meth)acryloyloxybutyltrimellitate, 4-(meth)acryloyloxyhexyltrimellitate, 4-(meth)acryloyloxydecyltrimellitate, 2-(meth)acryloyloxyethyl-3'-(meth)acryloyloxy-2'-(3,4-dicarboxybenzoyloxy)propyl succinate, and acid anhydrides or acid halides of these.

Among these compounds, the monomer (B) having an acidic group is preferably a phosphoric acid group- or pyrophosphoric acid group-containing (meth)acrylic monomer, particularly a phosphoric acid group-containing (meth)acrylic monomer, because these monomers develop more desirable adhesive properties to tooth structure. In view of the ability to exhibit high adhesive properties by showing high demineralization in the absence of an organic solvent, the monomer (B) having an acidic group is more preferably a divalent phosphoric acid group-containing (meth)acrylic monomer having a C6 to C20 alkyl or alkylene group as a backbone within the molecule, even more preferably a divalent phosphoric acid group-containing (meth)acrylic monomer having a C8 to C12 alkylene group as a backbone within the molecule (e.g., 10-methacryloyloxydecyl dihydrogen phosphate).

The monomer (B) having an acidic group may be used alone, or two or more thereof may be used in combination. Excessively high or low contents of monomer (B) having an acidic group may decrease the adhesive properties. In this respect, the content of monomer (B) having an acidic group preferably ranges from 1 to 50 parts by mass, more preferably 3 to 40 parts by mass, even more preferably 5 to 30 parts by mass in total 100 parts by mass of the polymerizable components in the dental composition.

The monomer (B) having an acidic group has a molecular weight of preferably 4,000 or less, more preferably 3,000 or less, even more preferably 2,000 or less.

Monomer (C) Having No Acidic Group and Having a Molecular Weight of Less than 5,000

The monomer (C) having no acidic group and having a molecular weight of less than 5,000 (hereinafter, referred to as "monomer (C) having no acidic group") can be classified into a hydrophobic monomer (C-1) having no acidic group and having a molecular weight of less than 5,000, and a hydrophilic monomer (C-2) having no acidic group and having a molecular weight of less than 5,000.

Hydrophobic Monomer (C-1) Having No Acidic Group and Having a Molecular Weight of Less than 5,000

The hydrophobic monomer (C-1) having no acidic group and having a molecular weight of less than 5,000 (hereinafter, referred to as "hydrophobic monomer (C-1)") improves properties such as the mechanical strength and ease of handling of the dental composition. The hydrophobic monomer (C-1) is preferably a radical monomer having no acidic group but having a polymerizable group. In view of ease of radical polymerization, the polymerizable group is preferably a (meth)acryl group and/or a (meth)acrylamide group. Here, "hydrophobic monomer (C-1)" means a monomer having a molecular weight of less than 5,000, and a solubility at 25° C. of less than 10 mass % in water. Examples include crosslinkable monomers such as aromatic compound-based bifunctional monomers, aliphatic compound-based bifunctional monomers, and tri- and higher-functional monomers.

Examples of the aromatic compound-based bifunctional monomers include 2,2-bis((meth)acryloyloxyphenyl)propane, 2,2-bis[4-(3-(meth)acryloyloxy-2-hydroxypropoxy)phenyl]propane, 2,2-bis(4-(meth)acryloyloxyethoxyphenyl)propane, 2,2-bis(4-(meth)acryloyloxypolyethoxyphenyl)propane, 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth)acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, and 2,2-bis(4-(meth)acryloyloxyisopropoxyphenyl)propane. Preferred are 2,2-bis[4-(3-methacryloyloxy-2-hydroxypropoxy)phenyl]propane (commonly known as "Bis-GMA"), 2,2-bis(4-(meth)acryloyloxyethoxyphenyl)propane, 2,2-bis(4-methacryloyloxypolyethoxyphenyl)propane (average number of moles of ethoxy group added is 2.6; commonly known as "D-2.6E"), 2,2-bis(4-(meth)acryloyloxydiethoxyphenyl)propane, 2,2-bis(4-(meth)acryloyloxytriethoxyphenyl)propane, 2,2-bis(4-(meth)acryloyloxytetraethoxyphenyl)propane, and 2,2-bis(4-(meth)acryloyloxypentaethoxyphenyl)propane.

Examples of the aliphatic compound-based bifunctional monomers include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth)acrylate, neopentyl glycol di(meth)acrylate, 1,3-butanediol di(meth)acrylate, 1,5-pentanediol di(meth)acrylate, 1,6-hexanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl)di(meth)acrylate, N-methacryloyloxyethylacrylam ide, and N-methacryloyloxypropylamide. Preferred are triethylene glycol diacrylate, triethylene glycol dimethacrylate (commonly known as "3G"), neopentyl glycol di(meth)acrylate, 1,2-bis(3-methacryloyloxy-2-hydroxypropoxy)ethane, 2,2,4-trimethylhexamethylenebis(2-carbamoyloxyethyl)dimethacrylate (commonly known as "UDMA"), 1,10-decanediol dimethacrylate (commonly known as "DD"), 2,2,4-trimethylhexamethylenebis(2-carbamoyloxyethyl)dimethacrylate, and N-methacryloyloxyethylacrylam ide (commonly known as "MAEA").

Examples of the tri- and higher-functional monomers include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetra(meth)acrylate, and 1,7-diacryloyloxy-2,2,6,6-tetra(meth)acryloyloxymethyl-4-oxaheptane. Preferred is N,N-(2,2,4-trimethylhexamethylene)bis[2-(aminocarboxy)propane-1,3-diol]tetramethacrylate.

In view of mechanical strength and ease of handling, preferred for use as hydrophobic monomer (C-1) are aromatic compound-based bifunctional monomers and aliphatic compound-based bifunctional monomers. Preferred as aromatic compound-based bifunctional monomers are Bis-GMA and D-2.6E. Preferred as aliphatic compound-based bifunctional monomers are glycerol di(meth)acrylate, 3G, neopentyl glycol di(meth)acrylate, 1,6-hexanediol di(meth)acrylate, DD, 1,2-bis(3-methacryloyloxy-2-hydroxypropoxy)ethane, UDMA, and MAEA.

In view of initial adhesion to tooth structure, bond durability, and mechanical strength, the hydrophobic monomer (C-1) is more preferably Bis-GMA, D-2.6E, 3G, UDMA, DD, or MAEA, even more preferably D-2.6E, DD, or MAEA.

The hydrophobic monomer (C-1) may be contained alone, or two or more thereof may be used in combination. When the content of hydrophobic monomer (C-1) is excessively high, the penetrability and adhesion of the composition to tooth structure may decrease, whereas the effect to improve mechanical strength may become insufficient with excessively low contents of hydrophobic monomer (C-1). In this respect, the content of hydrophobic monomer (C-1) preferably ranges from 20 to 99 parts by mass, more preferably 40 to 99 parts by mass, even more preferably 60 to 99 parts by mass relative to total 100 parts by mass of the polymerizable components in the dental composition.

Hydrophilic Monomer (C-2) Having No Acidic Group and Having a Molecular Weight of Less than 5,000

It is preferable that a dental composition of the present invention additionally comprise a hydrophilic monomer (C-2) having no acidic group and having a molecular weight of less than 5,000 (hereinafter, referred to as "hydrophilic monomer (C-2)"). The hydrophilic monomer (C-2) promotes penetration of the components of the dental composition into tooth structure. The hydrophilic monomer (C-2) itself also penetrates into tooth structure, and adheres to the organic component (collagen) in the tooth structure. The hydrophilic monomer (C-2) is preferably a radical monomer having no acidic group but having a polymerizable group. In view of ease of radical polymerization, the polymerizable group is preferably a (meth)acryl group and/or a (meth)acrylamide group. Here, "hydrophilic monomer (C-2)" means a monomer having a molecular weight of less than 5,000, and a solubility at 25° C. of 10 mass % or more in water. Preferably, the hydrophilic monomer (C-2) is one having a solubility at 25° C. of 30 mass % or more in water, more preferably one that can dissolve in water in any desired fractions at 25° C. The hydrophilic monomer (C-2) is preferably one having a hydrophilic group such as a hydroxyl group, an oxymethylene group, an oxyethylene group, an oxypropylene group, or an amide group. Examples of such monomers include hydrophilic monofunctional (meth)acrylate monomers such as 2-hydroxyethyl (meth) acrylate, 3-hydroxypropyl (meth)acrylate, 2-hydroxypropyl (meth)acrylate, 1,3-dihydroxypropyl (meth)acrylate, 2,3-dihydroxypropyl (meth)acrylate, 2-((meth)acryloyloxy)ethyltrimethylammonium chloride, and polyethylene glycol di(meth)acrylate (number of oxyethylene groups is 9 or more); and monofunctional (meth)acrylamide monomers such as N-methylol(meth)acrylamide, N-hydroxyethyl (meth)acrylamide, N,N-bis(2-hydroxyethyl)(meth)acrylamide, N-methoxymethyl(meth)acrylamide, N-ethoxymethyl (meth)acrylamide, diacetone(meth)acrylamide, 4-(meth) acryloylmorpholine, N-trihydroxymethyl-N-methyl(meth) acrylamide, N,N-dimethylacrylamide, and N,N-diethylacrylamide.

In view of adhesive properties to tooth structure, preferred as hydrophilic monomer (C-2) are 2-hydroxyethyl (meth) acrylate, 2,3-dihydroxypropyl (meth)acrylate, diacetone (meth)acrylamide, and hydrophilic monofunctional (meth) acrylamide monomers. More preferred are 2-hydroxyethyl (meth)acrylate, N,N-dimethylacrylamide, and N,N-diethylacrylamide. The hydrophilic monomer (C-2) may be contained alone, or two or more thereof may be used in combination.

In the present invention, the effect to improve adhesion may become insufficient when the content of hydrophilic monomer (C-2) is excessively low, whereas excessively high contents of hydrophilic monomer (C-2) may cause a decrease of mechanical strength. In this respect, the content of hydrophilic monomer (C-2) preferably ranges from 0 to 50 parts by mass, more preferably 0 to 40 parts by mass, even more preferably 0 to 30 parts by mass relative to total 100 parts by mass of the polymerizable components in the dental composition. The content of hydrophilic monomer (C-2) may be 0 part by mass.

The molecular weight of the monomer (C) having no acidic group is preferably 4,000 or less, more preferably 3,000 or less, even more preferably 2,000 or less, irrespective of whether the monomer (C) having no acidic group is a hydrophobic monomer (C-1) or a hydrophilic monomer (C-2).

Polymerization Initiator (D)

The polymerization initiator (D) can be broadly classified into photopolymerization initiator and chemical polymerization initiator, with the photopolymerization initiator further divided into water-soluble photopolymerization initiator (D-1) and water-insoluble photopolymerization initiator (D-2). The polymerization initiator (D) may be solely a water-soluble photopolymerization initiator (D-1) or a water-insoluble photopolymerization initiator (D-2), or a combination of water-soluble photopolymerization initiator (D-1) and water-insoluble photopolymerization initiator (D-2).

Water-Soluble Photopolymerization Initiator (D-1)

The water-soluble photopolymerization initiator (D-1) can achieve high bond strength by improving the polymerization curability at the hydrophilic tooth interface. The water-soluble photopolymerization initiator (D-1) has a solubility in water of 10 g/L or more, preferably 15 g/L or more, more preferably 20 g/L or more, even more preferably 25 g/L or more at 25° C. When the solubility is less than 10 g/L, the water-soluble photopolymerization initiator (D-1) does not sufficiently dissolve in water in tooth structure at the bond interface, and cannot sufficiently develop the polymerization promoting effect.

Examples of the water-soluble photopolymerization initiator (D-1) include water-soluble acylphosphine oxides, water-soluble thioxanthones, and α-hydroxyalkylacetophenones. The α-hydroxyalkylacetophenones may be, for example, compounds having a (poly)ethylene glycol chain introduced into the hydroxyl groups of 1-[4-(2-hydroxyethoxy)-phenyl]-2-hydroxy-2-methyl-1-propan-1-one, compounds having a (poly)ethylene glycol chain introduced into the hydroxyl group and/or phenyl group of 1-hydroxycyclohexyl phenyl ketone, compounds having $-OCH_2COO^-Na^+$ introduced into the phenyl group of 1-hydroxycyclohexyl phenyl ketone, compounds having a (poly)ethylene glycol chain introduced into the hydroxyl group and/or phenyl group of 2-hydroxy-2-methyl-1-phenylpropan-1-one, and compounds having $-OCH_2COO^-Na^+$ introduced into the phenyl group of 2-hydroxy-2-methyl-1-phenylpropan-1-one. Other examples of the water-soluble photopolymerization initiator (D-1) include quaternary ammonium compounds prepared by quaternization of the amino group of α-aminoalkylphenones, such as 2-methyl-1[4-(methylthio) phenyl]-2-morpholinopropan-1-one, and 2-benzyl-2-dimethylamino-1-(4-morpholinophenyl)butanone-1.

The water-soluble thioxanthones may be any of, for example, 2-hydroxy-3-(9-oxo-9H-thioxanthen-4-yloxy)-N,N,N-trimethyl-1-propaneaminium chloride, 2-hydroxy-3-(1-methyl-9-oxo-9H-thioxanthen-4-yloxy)-N,N,N-trimethyl-1-propaneaminium chloride, 2-hydroxy-3-(9-oxo-9H-thioxanthen-2-yloxy)-N,N,N-trimethyl-1-propaneaminium chloride, 2-hydroxy-3-(3,4-dimethyl-9-oxo-9H-thioxanthen-2-yloxy)-N,N,N-trimethyl-1-propaneaminium chloride, 2-hydroxy-3-(3,4-dimethyl-9H-thioxanthen-2-yloxy)-N,N,N-trimethyl-1-propaneaminium chloride, and 2-hydroxy-3-(1,3,4-trimethyl-9-oxo-9H-thioxanthen-2-yloxy)-N,N,N-trimethyl-1-propaneaminium chloride.

The water-soluble acylphosphine oxides may be, for example, acylphosphine oxides represented by the following general formula (1) or (2).

[Chem. 1]

(1)

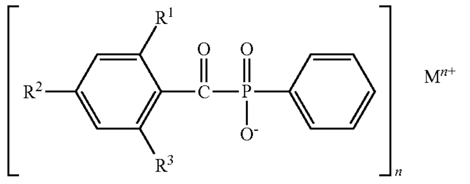

[Chem. 2]

(2)

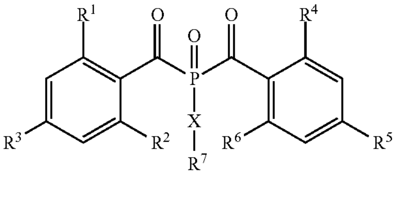

In the formulae, $R^1$, $R^2$, $R^3$, $R^4$, $R^5$, and $R^6$ are each independently a C1 to C4 linear or branched alkyl group or a halogen atom, M is a hydrogen ion, an alkali metal ion, an alkali earth metal ion, a magnesium ion, a pyridinium ion (the pyridine ring may have a substituent), or an ammonium ion represented by $HN^+R^8R^9R^{10}$ (where $R^8$, $R^9$, and $R^{10}$ are each independently an organic group or a hydrogen atom), n is 1 or 2, X is a C1 to C4 linear or branched alkylene group, $R^7$ represents $-CH(CH_3)COO(C_2H_4O)_pCH_3$, where p is an integer of 1 to 1,000.

The alkyl group represented by $R^1$, $R^2$, $R^3$, $R^4$, $R^5$, and $R^6$ is not particularly limited, as long as it is C1 to C4 linear or branched alkyl. Examples include methyl, ethyl, n-propyl, isopropyl, n-butyl, isobutyl, sec-butyl, 2-methylpropyl, and tert-butyl. The alkyl group represented by $R^1$, $R^2$, $R^3$, $R^4$, $R^5$, and $R^6$ is preferably a C1 to C3 linear alkyl group, preferably methyl or ethyl, more preferably methyl. Examples of the alkylene group represented by X include a methylene group, an ethylene group, an n-propylene group, an isopropylene group, and an n-butylene group. The alkylene group represented by X is preferably a C1 to C3 linear alkylene group, more preferably a methylene group or an ethylene group, even more preferably a methylene group.

Examples of the substituent of the pyridine ring when M is a pyridinium ion include halogen atoms (a fluorine atom, a chlorine atom, a bromine atom, an iodine atom), a carboxy group, a C2 to C6 linear or branched acyl group, a C1 to C6 linear or branched alkyl group, and a C1 to C6 linear or branched alkoxy group. Preferably, M is an alkali metal ion, an alkali earth metal ion, a magnesium ion, a pyridinium ion (the pyridine ring may have a substituent), or an ammonium ion represented by $HN^+R^8R^9R^{10}$ (the symbols have the same meaning as above). Examples of the alkali metal ion include a lithium ion, a sodium ion, a potassium ion, a rubidium ion, and a cesium ion. Examples of the alkali earth metal ion include a calcium ion, a strontium ion, a barium ion, and a radium ion. The organic group represented by $R^8$, $R^9$, and $R^{10}$ may be the same group exemplified above for the substituent of the pyridine ring (excluding a halogen atom).

In view of storage stability and shade stability in the composition, particularly preferred are compounds in which $R^1$, $R^2$, $R^3$, $R^4$, $R^5$, and $R^6$ are all methyl groups. Examples of $M^{n+}$ include $Li^+$, $Na^+$, $K^+$, $Ca^{2+}$, $Mg^{2+}$, and ammonium ions derived from various amines. Examples of the amines include ammonia, trimethylamine, diethylamine, dimethylaniline, ethylenediamine, triethanolamine, N,N-dimethylaminomethacrylate, N,N-dimethylaminobenzoic acid and alkyl esters thereof, N,N-diethylaminobenzoic acid and alkyl esters thereof, and N,N-bis(2-hydroxyethyl)-p-toluidine. In view of adhesive properties, p in $R^7$ is preferably 1 or more, more preferably 2 or more, even more preferably 3 or more, particularly preferably 4 or more, and is preferably 1,000 or less, more preferably 100 or less, even more preferably 75 or less, particularly preferably 50 or less.

Particularly preferably, the water-soluble acylphosphine oxides are compounds represented by general formula (1) and in which M is Li, and compounds represented by general formula (2) and in which the moiety corresponding to the group represented by $R^7$ is synthesized from polyethylene glycol methylether methacrylate having a molecular weight of 950.

The water-soluble acylphosphine oxides having such structures can be synthesized according to known methods, and some are available as commercially available products. For example, the methods disclosed in JP 57(1982)-197289 A and WO2014/095724 can be used for the synthesis of the water-soluble acylphosphine oxides. The water-soluble photopolymerization initiator (D-1) may be used alone, or two or more thereof may be used in combination.

The water-soluble photopolymerization initiator (D-1) may be dissolved in the dental composition, or may be dispersed in the form of a powder in the composition, provided that the water-soluble photopolymerization initiator (D-1) can dissolve in water at the surface of the tooth structure (moist body), and can selectively increase the polymerization curability at the bond interface and inside the resin-impregnated layer.

When the water-soluble photopolymerization initiator (D-1) is dispersed in the form of a powder, the average particle diameter is preferably 500 μm or less, more preferably 100 μm or less, even more preferably 50 μm or less because the water-soluble photopolymerization initiator (D-1) tends to precipitate when the average particle diameter is excessively large. The average particle diameter is preferably 0.01 μm or more because the specific surface area of the powder overly increases, and the amount of powder that can be dispersed in the composition decreases when the average particle diameter is excessively small. Taken together, the average particle diameter of water-soluble photopolymerization initiator (D-1) preferably ranges from 0.01 to 500 μm, more preferably 0.01 to 100 μm, even more preferably 0.01 to 50 μm.

The average particle diameter of a powder of water-soluble photopolymerization initiator (D-1) can be determined by taking an electron micrograph of at least 100 particles, and calculating the volume average particle diameter from the captured image after an image analysis performed with image-analyzing software (Mac-View, manufactured by Mountech Co., Ltd.).

The shape of the water-soluble photopolymerization initiator (D-1) when dispersed in the form of a powder is not particularly limited, and may be any of various shapes, including, for example, spherical, stylus, plate-like, and crushed shapes. The water-soluble photopolymerization initiator (D-1) can be prepared using a known method such as pulverization, freeze drying, or reprecipitation. In view of the average particle diameter of the powder obtained, freeze drying and reprecipitation are preferred, and freeze drying (method 1) is more preferred.

In view of curability and other properties of the dental composition obtained, the content of water-soluble photopolymerization initiator (D-1) is preferably 0.01 to 20 parts by mass relative to total 100 parts by mass of the polymerizable components in the dental composition. In view of providing high initial adhesion and bond durability and reducing polymerization shrinkage stress, the content of water-soluble photopolymerization initiator (D-1) is more preferably 0.05 to 10 parts by mass, even more preferably 0.1 to 5 parts by mass relative to total 100 parts by mass of the polymerizable components in the dental composition. When the content of water-soluble photopolymerization initiator (D-1) is less than 0.01 parts by mass, polymerization may fail to sufficiently proceed at the bond interface, and the bond strength may decrease. When the content of water-soluble photopolymerization initiator (D-1) is more than 20 parts by mass, it may not be possible to obtain a sufficient bond strength when the water-soluble photopolymerization initiator (D-1) has low polymerization performance, in addition to making it difficult to sufficiently dissolve, disperse, or diffuse water-soluble photopolymerization initiator (D-1) in the dental composition.

Water-Insoluble Photopolymerization Initiator (D-2)

In view of curability, a dental composition of the present invention may comprise a water-insoluble photopolymerization initiator (D-2) having a solubility in water of less than 10 g/L at 25° C. (hereinafter, referred to as "water-insoluble photopolymerization initiator (D-2)"), other than the water-soluble photopolymerization initiator (D-1). The water-insoluble photopolymerization initiator (D-2) used in the present invention may use a known photopolymerization initiator. The water-insoluble photopolymerization initiator (D-2) may be contained alone, or two or more thereof may be contained in combination.

Examples of the water-insoluble photopolymerization initiator (D-2) include (bis)acylphosphine oxides, thioxanthones, ketals, α-diketones, coumarins, anthraquinones, benzoin alkyl ether compounds, and α-aminoketone compounds, excluding those exemplified for water-soluble photopolymerization initiator (D-1).

Examples of acylphosphine oxides in the (bis)acylphosphine oxides include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di(2,6-dimethylphenyl)phosphonate. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl) phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis (2,5,6-trimethylbenzoyl)-2,4,4-trimethylpentylphosphine oxide.

Examples of the thioxanthones include thioxanthone, and 2-chlorothioxanthen-9-one.

Examples of the ketals include benzyl dimethyl ketal, and benzyl diethyl ketal.

Examples of the α-diketones include diacetyl, benzyl, dl-camphorquinone, 2,3-pentadione, 2,3-octadione, 9,10-phenanthrenequinone, 4,4'-oxybenzyl, and acenaphthenequinone. Particularly preferred is dl-camphorquinone for its maximum absorption wavelength occurring in the visible light region.

Examples of the coumarin compounds include compounds mentioned in JP 9(1997)-3109 A and JP 10(1998)-245525 A, including, for example, 3,3'-carbonylbis(7-diethylaminocoumarin), 3-(4-methoxybenzoyl)coumarin, 3-thienoylcoumarin, 3-benzoyl-5,7-diethylaminocoumarin), 3-benzoyl-7-methoxycoumarin, 3-benzoyl-6-methoxycoumarin, 3-benzoyl-8-methoxycoumarin, 3-benzoylcoumarin, 7-methoxy-3-(p-nitrobenzoyl)coumarin, 3-(p-nitrobenzoyl) coumarin, 3,5-carbonylbis(7-methoxycoumarin), 3-benzoyl-6-bromocoumarin, 3,3'-carbonylbiscoumarin, 3-benzoyl-7-dimethylaminocoumarin, 3-benzoylbenzo[f] coumarin, 3-carboxycoumarin, 3-carboxy-7-methoxycoumarin, 3-ethoxycarbonyl-6-methoxycoumarin, 3-ethoxycarbonyl-8-methoxycoumarin, 3-acetylbenzo[f] coumarin, 3-benzoyl-6-nitrocoumarin, 3-benzoyl-7-diethylaminocoumarin, 7-dimethylamino-3-(4-methoxybenzoyl) coumarin, 7-diethylamino-3-(4-methoxybenzoyl)coumarin, 7-diethylamino-3-(4-diethylamino)coumarin, 7-methoxy-3-(4-methoxybenzoyl)coumarin, 3-(4-nitrobenzoyl)benzo[f] coumarin, 3-(4-ethoxycinnamoyl)-7-methoxycoumarin, 3-(4-dimethylaminocinnamoyl)coumarin, 3-(4-diphenylaminocinnamoyl)coumarin, 3-[(3-dimethylbenzothiazol-2-ylidene)acetyl]coumarin, 3-[(1-methylnaphtho[1,2-d]thiazol-2-ylidene)acetyl]coumarin, 3,3'-carbonylbis(6-methoxycoumarin), 3,3'-carbonylbis(7-acetoxycoumarin), 3,3'-carbonylbis(7-dimethylaminocoumarin), 3-(2-benzothiazolyl)-7-(diethylamino)coumarin, 3-(2-benzothiazolyl)-7-(dibutylamino)coumarin, 3-(2-benzoimidazolyl)-7-(diethylamino)coumarin, 3-(2-benzothiazolyl)-7-(dioctylamino) coumarin, 3-acetyl-7-(dimethylamino)coumarin, 3,3'-carbonylbis(7-dibutylaminocoumarin), 3,3'-carbonyl-7-diethylaminocoumarin-7'-bis(butoxyethyl)aminocoumarin, 10-[3-[4-(dimethylamino)phenyl]-1-oxo-2-propenyl]-2,3,6,7-tetrahydro-1,1,7,7-tetramethyl-1H,5H,11H-[1]benzopyrrano[6,7,8-ij]quinolizin-11-one, and 10-(2-benzothiazolyl)-2,3,6,7-tetrahydro-1,1,7,7-tetramethyl-1H,5H,11H-[1] benzopyrrano[6,7,8-ij]quinolizin-11-one.

Particularly preferred among these coumarin compounds are 3,3'-carbonylbis(7-diethylaminocoumarin) and 3,3'-carbonylbis(7-dibutylaminocoumarin).

Examples of the anthraquinones include anthraquinone, 1-chloroanthraquinone, 2-chloroanthraquinone, 1-bromoanthraquinone, 1,2-benzanthraquinone, 1-methylanthraquinone, 2-ethylanthraquinone, and 1-hydroxyanthraquinone.

Example of the benzoin alkyl ether compounds include benzoin methyl ether, benzoin ethyl ether, benzoin isopropyl ether, and benzoin isobutyl ether.

Examples of the α-aminoketone compounds include 2-methyl-1-[4-(methylthio)phenyl]-2-morpholinopropan-1-one.

The water-insoluble photopolymerization initiator (D-2) is preferably at least one selected from the group consisting of a (bis)acylphosphine oxide, an α-diketone, and a coumarin compound. In this way, a dental composition can be obtained that has desirable photocurability both in the visible light region and the near ultraviolet region, and that shows sufficient photocurability regardless of whether the light source used is a halogen lamp, a light emitting diode (LED), or a xenon lamp.

The content of water-insoluble photopolymerization initiator (D-2) is not particularly limited. However, in view of curability and other properties of the composition obtained, the content of water-insoluble photopolymerization initiator (D-2) preferably ranges from 0.01 to 10 parts by mass, more preferably 0.05 to 7 parts by mass, even more preferably 0.1 to 5 parts by mass relative to total 100 parts by mass of the polymerizable components in the dental composition. When the content of water-insoluble photopolymerization initiator (D-2) is more than 10 parts by mass, it may not be possible to obtain a sufficient bond strength when the polymerization initiator itself has low polymerization performance, in addition to raising a possibility of precipitation from the dental composition.

In the present invention, the mass ratio of water-soluble photopolymerization initiator (D-1) and water-insoluble photopolymerization initiator (D-2) [(D-1):(D-2)] is preferably 10:1 to 1:10, more preferably 7:1 to 1:7, even more preferably 5:1 to 1:5, particularly preferably 3:1 to 1:3. When the fraction of water-soluble photopolymerization initiator (D-1) in the mass ratio exceeds 10:1, the curability of the dental composition itself decreases, and the dental composition may have difficulty in exhibiting high bond strength. When the fraction of water-insoluble photopolymerization initiator (D-2) in the mass ratio exceeds 1:10, the dental composition may have difficulty in exhibiting high bond strength as a result of insufficient promotion of polymerization at the bond interface, though the curability of the dental composition itself increases.

Chemical Polymerization Initiator

A dental composition of the present invention may additionally comprise a chemical polymerization initiator, for which an organic peroxide is preferred. The organic peroxide used as the chemical polymerization initiator is not particularly limited, and known organic peroxides may be used. Typical examples of such organic peroxides include ketoneperoxides, hydroperoxides, diacyl peroxides, dialkyl peroxides, peroxyketals, peroxyesters, and peroxy dicarbonates. Specific examples of these organic peroxides include those mentioned in WO2008/087977.

Polymerization Accelerator (E)

In another embodiment, a polymerization accelerator (E) is used with the water-insoluble photopolymerization initiator (D-2) and/or the chemical polymerization initiator. Examples of the polymerization accelerator (E) used in the present invention include amines, sulfinic acid and salts thereof, borate compounds, derivatives of barbituric acid, triazine compounds, copper compounds, tin compounds, vanadium compounds, halogen compounds, aldehydes, thiol compounds, sulfites, bisulfites, and thiourea compounds.

The amines used as polymerization accelerator (E) can be categorized into aliphatic amines and aromatic amines. Examples of the aliphatic amines include primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine. In view of the curability and storage stability of the dental composition, preferred for use are tertiary aliphatic amines, and N-methyldiethanolamine and triethanolamine are more preferred.

Examples of the aromatic amines include N,N-bis(2-hydroxyethyl)-3,5-dimethylaniline, N,N-bis(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-diisopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, propyl 4-(N,N-dimethylamino)benzoate, n-butoxyethyl 4-(N,N-dimethylamino)benzoate, 2-(methacryloyloxy)ethyl 4-(N,N-dimethylamino)benzoate, 4-(N,N-dimethylamino)benzophenone, and butyl 4-(N,N-dimethylamino)benzoate. In view of the ability to impart desirable curability to the dental composition, it is preferable to use at least one selected from the group consisting of N,N-bis(2-hydroxyethyl)-p-toluidine, ethyl 4-(N, N-dimethylamino)benzoate, n-butoxyethyl 4-(N, N-dimethylamino)benzoate, and 4-(N,N-dimethylamino)benzophenone.

Specific examples of sulfinic acid and salts thereof, borate compounds, derivatives of barbituric acid, triazine compounds, copper compounds, tin compounds, vanadium compounds, halogen compounds, aldehydes, thiol compounds, sulfites, bisulfites, and thiourea compounds include those mentioned in WO2008/087977.

The polymerization accelerator (E) may be contained alone, or two or more thereof may be contained in combination. The content of the polymerization accelerator (E) used in the present invention is not particularly limited. However, in view of curability and other properties of the dental composition obtained, the content of polymerization accelerator (E) is preferably 0.001 to 30 parts by mass, more preferably 0.01 to 20 parts by mass, even more preferably 0.1 to 5 parts by mass relative to total 100 parts by mass of the polymerizable components in the dental composition. When the content of polymerization accelerator (E) is less than 0.001 parts by mass, polymerization may fail to proceed sufficiently, and this may lead to a decrease of adhesive properties. In this respect, the content of polymerization accelerator (E) is more preferably 0.01 parts by mass or more. When the content of polymerization accelerator (E) is more than 30 parts by mass, it may not be possible to obtain sufficient adhesive properties when the polymerization initiator itself has low polymerization performance, in addition to raising a possibility of precipitation from the dental composition. In this respect, the content of polymerization accelerator (E) is more preferably 20 parts by mass or less.

Filler (F)

A dental composition of the present invention may further comprise a filler (F), depending on the embodiment. Typically, the filler (F) can be broadly classified into organic fillers, inorganic fillers, and organic-inorganic composite fillers. Examples of the materials of the organic fillers include polymethylmethacrylate, polyethylmethacrylate, a methyl methacrylate-ethyl methacrylate copolymer, crosslinked polymethylmethacrylate, crosslinked polyethylmethacrylate, polyamides, polyvinyl chloride, polystyrene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used alone, or two or more thereof may be used as a mixture. The shape of the organic filler is not particularly limited, and the particle diameter of the filler may be appropriately selected for use. In view of considerations such as the ease of handling and mechanical strength of the dental composition obtained, the average particle diameter of the organic filler is preferably 0.001 to 50 μm, more preferably 0.001 to 10 μm.

Examples of the materials of the inorganic fillers include quartz, silica, alumina, silica-titania, silica-titania-barium oxide, silica-zirconia, silica-alumina, lanthanum glass, borosilicate glass, soda glass, barium glass, strontium glass, glass-ceramics, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, strontium calcium fluoroaluminosilicate glass, ytterbium oxide, and silica-coated ytterbium fluoride. These may be used alone, or two or more thereof may be used as a mixture. The shape of the inorganic filler is not particularly limited, and the particle diameter of the filler may be appropriately selected for use. In view of considerations such as the ease of handling and mechanical strength of the composition obtained, the average particle diameter of the inorganic filler is preferably 0.001 to 50 μm, more preferably 0.001 to 10 μm.

The inorganic filler may be, for example, an irregularly shaped filler or a spherical filler. In view of improving the mechanical strength of the composition, the inorganic filler used is preferably a spherical filler. Another advantage of using a spherical filler is that the dental composition of the present invention, when used as a self-adhesive dental composite resin, can produce a composite resin having desirable surface gloss. Here, the spherical filler is a filler having an average uniformity of 0.6 or more as measured for round-shaped particles observed in a unit field of an electron micrograph of filler by dividing a particle diameter along a direction orthogonal to the maximum diameter by the maximum diameter. The spherical filler has an average particle diameter of preferably 0.05 to 5 μm. When the average particle diameter is less than 0.05 μm, the mechanical strength may decrease as a result of a decrease of the filling rate of the spherical filler in the composition. When the average particle diameter is more than 5 μm, the spherical filler has a reduced surface area, and the dental composition may fail to produce a cured product having high mechanical strength.

In order to adjust the flowability of the dental composition, the inorganic filler may be used after an optional surface treatment with a known surface treatment agent such as a silane coupling agent. Examples of the surface treatment agent include vinyltrimethoxysilane, vinyltriethoxysilane, vinyltrichlorosilane, vinyl tri(β-methoxyethoxy)silane, γ-methacryloyloxypropyltrimethoxysilane, 8-methacryloyloxyoctyltrimethoxysilane, 11-methacryloyloxyundecyltrimethoxysilane, γ-glycidoxypropyltrimethoxysilane, γ-mercaptopropyltrimethoxysilane, and γ-aminopropyltriethoxysilane.

The organic-inorganic composite filler used in the present invention is a filler obtained by adding a polymerizable compound to the inorganic filler, polymerizing the mixture in paste form, and pulverizing the polymerized filler. The organic-inorganic composite filler may be, for example, a TMPT filler (a filler obtained by mixing trimethylolpropane methacrylate and a silica filler, and pulverizing the mixture after polymerization). The shape of the organic-inorganic composite filler is not particularly limited, and may be determined by appropriately selecting the particle size of the filler. In view of properties such as the ease of handling and mechanical strength of the composition obtained, the organic-inorganic composite filler has an average particle diameter of preferably 0.001 to 50 μm, more preferably 0.001 to 10 μm.

In this specification, the average particle diameter of filler can be determined using a laser diffraction scattering method or by observing particles with an electron microscope. Specifically, a laser diffraction scattering method is more convenient for the measurement of particles having a particle size of 0.1 μm or more, whereas electron microscopy is a more convenient method of particle size measurement for ultrafine particles of less than 0.1 μm. Here, 0.1 μm is a measured value by a laser diffraction scattering method.

As a specific example of a laser diffraction scattering method, the particle size may be measured by volume using, for example, a laser diffraction particle size distribution analyzer (SALD-2300, manufactured by Shimadzu Corporation) with a 0.2% sodium hexametaphosphate aqueous solution used as dispersion medium.

In electron microscopy, for example, particles may be photographed with an electron microscope (Model S-4000, manufactured by Hitachi), and the size of particles (at least 200 particles) observed in a unit field of the captured image may be measured using image-analyzing particle-size-distribution measurement software (Mac-View; Mountech Co., Ltd.). Here, the particle diameter is determined as an arithmetic mean value of the maximum and minimum lengths of particles, and the average primary particle diameter is calculated from the number of particles and the particle diameter.

In the present invention, two or more kinds of fillers of different materials having different particle size distributions and different forms may be mixed or combined for use. Unintended inclusion of non-filler particles as impurities is acceptable to such an extent that it is not detrimental to the effects of the present invention.

The content of the filler (F) used in the present invention is not particularly limited, and is preferably 0 to 2,000 parts by mass relative to total 100 parts by mass of the polymerizable components in the dental composition. The preferred content of filler (F) greatly differs in different embodiments. The preferred content of filler (F) suited for each embodiment is presented below in the specific embodiments of a dental composition of the present invention described below.

Fluorine-Ion Releasing Substance

A dental composition of the present invention may further comprise a fluorine-ion releasing substance. By containing a fluorine-ion releasing substance, the dental composition produced can impart acid resistance to tooth structure. Examples of the fluorine-ion releasing substance include metal fluorides such as sodium fluoride, potassium fluoride, sodium monofluorophosphate, lithium fluoride, and ytterbium fluoride. The fluorine-ion releasing substance may be used alone, or two or more thereof may be used in combination.

The dental composition may additionally comprise additives such as pH adjusters, polymerization inhibitors, thickeners, colorants, fluorescent agents, fragrances, and cross-linking agents (for example, polyvalent metal ion releasing components), provided such additives do not interfere with the effects of the present invention. These may be used alone, or two or more thereof may be used in combination. A dental composition of the present invention may also comprise anti-microbial substances such as cetylpyridinium chloride, benzalkonium chloride, (meth)acryloyloxydodecylpyridinium bromide, (meth)acryloyloxyhexadecylpyridinium chloride, (meth)acryloyloxydecylammonium chloride, and triclosan. A dental composition of the present invention may comprise a known dye or pigment as a colorant. The polyvalent metal ion releasing components are, for example, metal ion releasing components belonging to Group 3 and Group 13 of the periodic table. Examples of the metals belonging to Group 3 of the periodic table include yttrium, scandium, and lanthanoids. Examples of the metals belonging to Group 13 of the periodic table include aluminum, gallium, and indium. In view of moderately reducing the crosslink density in the polymer matrix and not interfering with the polymerization shrinkage stress reducing effect of (meth)acrylic compound (A), a preferred embodiment of the present invention is, for example, a dental composition that does not contain a cross-linking agent, for example, a polyvalent metal ion releasing component, that forms an ionic crosslink with the monomer (B) having an acidic group.

The components of a dental composition of the present invention other than the (meth)acrylic compound (A), the monomer (B) having an acidic group, the monomer (C) having no acidic group, the polymerization initiator (D), the polymerization accelerator (E), the filler (F), and polymerization inhibitors and colorants are preferably less than 0.1 mass %, more preferably less than 0.01 mass %, even more preferably less than 0.001 mass %. A dental composition of the present invention is preferably one having a polymerization shrinkage stress of less than 10 MPa, more preferably less than 9.5 MPa, even more preferably less than 9.0 MPa. The method of measurement of polymerization shrinkage stress is as described in the EXAMPLES section below.

A dental composition of the present invention can be used for dental treatment as, for example, a self-adhesive dental composite resin, a dental bonding material, a dental cement, a pit and fissure sealant, a loose tooth fixing material, or an orthodontic bonding material. Particularly, a dental composition of the present invention is suited as a dental bonding material, a self-adhesive dental composite resin, or a dental cement. In such applications, a dental composition of the present invention may be provided in two bottles or two pastes of divided components. The following describes specific embodiments of different uses of a dental composition of the present invention.

Self-Adhesive Dental Composite Resin

A preferred embodiment of a dental composition of the present invention is, for example, a self-adhesive dental composite resin. When used as a self-adhesive dental composite resin, a dental composition of the present invention preferably comprises the (meth)acrylic compound (A), the monomer (B) having an acidic group, the monomer (C) having no acidic group, the polymerization initiator (D), the polymerization accelerator (E), and the filler (F). The polymerization initiator (D) is preferably a photopolymerization initiator, more preferably one comprising the water-soluble photopolymerization initiator (D-1) and the water-insoluble photopolymerization initiator (D-2). When used as a dental composite resin, a dental composition of the present invention may use a pretreatment agent. However, because a dental composition of the present invention has self-adhesive properties, a pretreatment agent is not essential, and it is not necessarily required to use a pretreatment agent. In this way, a self-adhesive dental composite resin can be provided that solely contains a dental composition of the present invention, with no pretreatment agent.

The content of each component in the self-adhesive dental composite resin is such that the dental composition comprises preferably 0.1 to 30 parts by mass of (meth)acrylic compound (A), 1 to 50 parts by mass of monomer (B) having an acidic group, and 1 to 98 parts by mass of monomer (C) having no acidic group, more preferably 0.5 to 25 parts by mass of (meth)acrylic compound (A), 1 to 80 parts by mass of monomer (B) having an acidic group, and 5 to 95 parts by mass of monomer (C) having no acidic group, even more preferably 1 to 20 parts by mass of (meth)acrylic compound (A), 3 to 40 parts by mass of monomer (B) having an acidic group, and 10 to 90 parts by mass of monomer (C) having no acidic group in total 100 parts by mass of the polymerizable components in the dental composition. Preferably, the dental composition comprises 0.001 to 30 parts by mass of polymerization initiator (D), 0.001 to 20 parts by mass of polymerization accelerator (E), and 50 to 2,000 parts by mass of filler (F), more preferably 0.05 to 10 parts by mass of polymerization initiator (D), 0.05 to 10 parts by mass of polymerization accelerator (E), and 100 to 1,500 parts by mass of filler (F) relative to total 100 parts by mass of the polymerizable components.

Dental Bonding Material

Another preferred embodiment of a dental composition of the present invention is, for example, a dental bonding material. A dental bonding material as a preferred embodiment of a dental composition of the present invention allows demineralization, penetration, and cure in one step. The dental bonding material may be a two-bottle type, which is used by mixing first and second components immediately before use, or a one-bottle type, which uses only one component. The one-bottle type is simpler to use, and has more merits in use. The dental bonding material may use, for example, a self-etching primer as pretreatment agent. The dental composition used for the dental bonding material preferably comprises the (meth)acrylic compound (A), the monomer (B) having an acidic group, the monomer (C) having no acidic group, the polymerization initiator (D), the polymerization accelerator (E), and the filler (F). Preferably, the polymerization initiator (D) is a photopolymerization initiator, more preferably one using the water-soluble photopolymerization initiator (D-1) and the water-insoluble photopolymerization initiator (D-2) in combination.

The content of each component in the dental bonding material is such that the dental composition comprises preferably 0.1 to 30 parts by mass of (meth)acrylic compound (A), 1 to 90 parts by mass of monomer (B) having an acidic group, and 1 to 98 parts by mass of monomer (C) having no acidic group, more preferably 0.5 to 25 parts by mass of (meth)acrylic compound (A), 5 to 80 parts by mass of monomer (B) having an acidic group, and 5 to 95 parts by mass of monomer (C) having no acidic group, even more preferably 1 to 20 parts by mass of (meth)acrylic compound (A), 5 to 70 parts by mass of monomer (B) having an acidic group, and 10 to 90 parts by mass of monomer (C) having no acidic group relative to total 100 parts by mass of the polymerizable components in the dental composition. Preferably, the dental composition comprises 0.001 to 30 parts by mass of polymerization initiator (D), 0.001 to 20 parts by mass of polymerization accelerator (E), and 0 to 100 parts by mass of filler (F), more preferably 0.05 to 10 parts by mass of polymerization initiator (D), 0.05 to 10 parts by mass of polymerization accelerator (E), and 1 to 75 parts by mass of filler (F) relative to total 100 parts by mass of the polymerizable components.

Dental Cement

Another preferred embodiment of a dental composition of the present invention is, for example, a dental cement. Preferred examples of the dental cement include resin cements, glass ionomer cements, and resin-reinforced glass ionomer cements. The dental cement may use, for example, a self-etching primer as pretreatment agent. When used as a dental cement, a dental composition of the present invention preferably comprises the (meth)acrylic compound (A), the monomer (B) having an acidic group, the monomer (C) having no acidic group, polymerization initiator (D), the polymerization accelerator (E), and the filler (F). Preferably, the polymerization initiator (D) is a chemical polymerization initiator, more preferably one using a chemical polymerization initiator and a photopolymerization initiator in combination. Preferably, the photopolymerization initiator uses the water-soluble photopolymerization initiator (D-1) and the water-insoluble photopolymerization initiator (D-2) in combination.

The content of each component in the dental cement is such that the dental composition preferably comprises 0.1 to 30 parts by mass of (meth)acrylic compound (A), 1 to 50 parts by mass of monomer (B) having an acidic group, and 1 to 98 parts by mass of monomer (C) having no acidic group, more preferably 0.5 to 25 parts by mass of (meth)acrylic compound (A), 1 to 80 parts by mass of monomer (B) having an acidic group, and 5 to 95 parts by mass of monomer (C) having no acidic group, even more preferably 1 to 20 parts by mass of (meth)acrylic compound (A), 3 to 40 parts by mass of monomer (B) having an acidic group, and 10 to 90 parts by mass of monomer (C) having no acidic group in total 100 parts by mass of the polymerizable components in the dental composition. Preferably, the dental composition comprises 0.001 to 30 parts by mass of polymerization initiator (D), 0.001 to 20 parts by mass of polymerization accelerator (E), and 50 to 2,000 parts by mass of filler (F), more preferably 0.05 to 10 parts by mass of polymerization initiator (D), 0.05 to 10 parts by mass of polymerization accelerator (E), and 100 to 1,500 parts by mass of filler (F) relative to total 100 parts by mass of the polymerizable components.

A dental composition of the present invention may comprise a solvent, depending on use. Examples of the solvent include water, and organic solvents. The organic solvents may be any known organic solvents, including, for example, alcohol solvents (such as methanol, ethanol, 1-propanol, and 2-propanol), acetone, methyl ethyl ketone, tetrahydrofuran, diethyl ether, diisopropyl ether, hexane, toluene, chloroform, ethyl acetate, and butyl acetate. Preferred are alcohol solvents. In an embodiment using an organic solvent, the content of organic solvent is preferably 1 to 2,000 parts by mass, more preferably 2 to 1,000 parts by mass, even more preferably 3 to 500 parts by mass relative to total 100 parts by mass of the polymerizable components. For example, when used as a self-adhesive dental composite resin or a dental cement, a dental composition of the present invention may be a dental composition containing no solvent. However, inclusion of trace amounts of moisture or organic solvent (for example, at most 3 mass % relative to the composition) is acceptable, provided that it does not cause problems such as improper or delayed cure. Some commercially available products that can be used as components (for example, colloidal silica) of a dental composition of the present invention contain water or organic solvent. When using such components, the product can be used for the preparation of a dental composition of the present invention after removing water or organic solvent to the acceptable limits.

In all of these preferred embodiments as self-adhesive dental composite resin, dental bonding material, and dental cement, the content of each component may be appropriately varied, and changes such as addition and deletion of any component may be made following the descriptions of the present specification.

The present invention encompasses embodiments combining the foregoing features, provided that such combinations made in various forms within the technical idea of the present invention can produce the effects of the present invention.

EXAMPLES

The following describes the present invention in greater detail by way of Examples. However, the present invention is not limited by the following Examples. It should also be noted that the combinations of the features described in the Examples below do not necessarily represent all the means necessary for solving the problems identified in the present invention. The components used in the following Examples and Comparative Examples, and the abbreviations and the structures of these components are presented below, along with the test methods used.

(Meth)Acrylic Compound (A)

UN-7700: Urethane acrylate (manufactured by Negami Chemical Industrial Co., Ltd.; viscosity: 300,000 to 750,000 cps/25° C.; weight-average molecular weight (Mw): 15,000 to 25,000; glass transition temperature (Tg): −41° C.; polyester backbone; number of acryl groups: 2; weight-average molecular weight per acryl group: 7,500 to 12,500)

UN-350: Urethane acrylate (manufactured by Negami Chemical Industrial Co., Ltd.; viscosity: ≥2,000,000 cps/25° C.; weight-average molecular weight (Mw): 12,500; glass transition temperature (Tg): −57° C.; polyester backbone; number of acryl groups: 2; weight-average molecular weight per acryl group: 6,250)

UN-353: Urethane acrylate (manufactured by Negami Chemical Industrial Co., Ltd.; viscosity: ≥2,000,000 cps/25° C.; weight-average molecular weight (Mw): 5,000; glass transition temperature (Tg): 10° C.; polyester backbone; number of acryl groups: 2; weight-average molecular weight per acryl group: 2,500)

(Meth)Acrylic Compound

UN-2600: Urethane acrylate (manufactured by Negami Chemical Industrial Co., Ltd.; viscosity: 75,000 to 90,000 cps/25° C.; weight-average molecular weight (Mw): 2,500; glass transition temperature (Tg): −1° C.; number of acryl groups: 2; weight-average molecular weight per acryl group: 1,250)

EBECRYL 8807: Urethane acrylate (manufactured by Daicel Corporation; viscosity: 8,000 cps/60° C.; weight-average molecular weight (Mw): 1,000; glass transition temperature (Tg): 32° C.; number of acryl groups: 2; weight-average molecular weight per acryl group: 500)

Monomer (B) having an acidic group and a molecular weight of less than 5,000

MDP: 10-Methacryloyloxydecyl Dihydrogen Phosphate

Monomer (C) having no acidic group and having a molecular weight of less than 5,000

D-2.6E: 2,2-Bis(4-methacryloyloxypolyethoxyphenyl) propane (average number of moles of ethoxy group added is 2.6)

DD: 1,10-Decanediol dimethacrylate

MAEA: N-Methacryloyloxyethylacrylamide

Polymerization Initiator (D)

Water-Soluble Photopolymerization Initiator (D-1)

Li-TPO: Lithium phenyl(2,4,6-trimethylbenzoyl)phosphinate (compound represented by the following formula (3))

[Chem. 3]

(3)

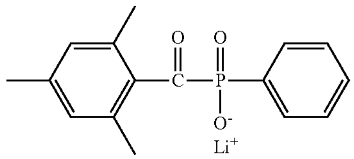

Water-Insoluble Photopolymerization Initiator (D-2)

CQ: dl-Camphorquinone

Polymerization Accelerator (E)

DABE: Ethyl 4-(N,N-dimethylamino)benzoate

Filler (F)

Inorganic filler 1: Fine silica particle Aerosil R972 manufactured by Nippon Aerosil Co., Ltd.; average particle diameter: 16 nm Inorganic Filler 2: Silane-Treated Silica Stone Powder A silica stone powder (manufactured by Nitchitsu Co., Ltd. under the trade name Hi-Silica) was pulverized with a ball mill to obtain a pulverized silica stone powder. The pulverized silica stone powder had an average particle diameter of 2.2 μm as measured with a laser diffraction particle size distribution analyzer (Model SALD-2300 manufactured by Shimadzu Corporation). The pulverized silica stone powder was surface treated with 4 parts by mass of γ-methacryloyloxypropyltrimethoxysilane against 100 parts by mass of the pulverized silica stone powder, using an ordinary method. This produced a silane-treated silica stone powder.

Inorganic Filler 3: Silane-Treated Barium Glass Powder

A barium glass (E-3000 manufactured by Esstech under this trade name) was pulverized with a ball mill to obtain a barium glass powder. The barium glass powder had an average particle diameter of 2.4 μm as measured with a laser diffraction particle size distribution analyzer (Model SALD-2300 manufactured by Shimadzu Corporation). The barium glass powder was surface treated with 3 parts by mass of γ-methacryloyloxypropyltrimethoxysilane against 100 parts by mass of the barium glass powder, using an ordinary method. This produced a silane-treated barium glass powder.

Other

BHT 2,6-Di-t-butyl-4-methylphenol (Stabilizer, or Polymerization Inhibitor)

EXAMPLES AND COMPARATIVE EXAMPLES: APPLICATION OF DENTAL COMPOSITION AS SELF-ADHESIVE DENTAL COMPOSITE RESIN

Examples 1 to 8 and Comparative Examples 1 to 4

The foregoing components were mixed and kneaded at ordinary temperature as shown in Tables 1 and 2 to prepare self-adhesive dental composite resins of Examples 1 to 8 and dental composite resins of Comparative Examples 1 to 4. The self-adhesive dental composite resins were measured for polymerization shrinkage stress, flexural modulus, flexural strength, and shear bond strength to enamel, using the methods below. Tables 1 and 2 show the test results, along with the proportion of each component (parts by mass) of the self-adhesive dental composite resins of Examples and Comparative Examples.

Measurement of Polymerization Shrinkage Stress

A 5.0 mm-thick glass plate sandblasted with a 50 μm alumina powder was fitted with a stainless-steel washer (inner diameter 5.3 mm×0.8 mm thickness) after applying a release agent to the washer, and the composite resin of each Example and Comparative Example was filled into the washer. After removing the excess composite resin paste, a stainless-steel jig (Ø=5 mm) that had been separately subjected to sandblasting was held against the glass plate with the composite resin in between.

The sample was then irradiated with a dental LED photoirradiator (PenCure 2000, manufactured by J. Morita Corp. under this trade name) for 10 seconds from the glass plate side to cure the composite resin, and the polymerization shrinkage stress was measured with a universal testing machine (manufactured by Shimadzu Corporation). After three measurements, the mean value was calculated as polymerization shrinkage stress (N=3).

Evaluation of Flexural Properties

Strength was evaluated by conducting a flexure test in compliance with ISO4049:2009, specifically as follows. The dental composition (paste) was filled into a SUS die (measuring 2 mm in length, 25 mm in width, and 2 mm in thickness), and pressed between glass slides from top and bottom (2 mm×25 mm surface). Thereafter, light was applied through the glass slides from both sides to cure the dental composition. Here, light was applied at 5 points each side, 10 seconds at each point, using a dental LED photoirradiator (PenCure 2000, manufactured by J. Morita Corp.). The cured product was then tested in a flexure test at a span length of 20 mm and a crosshead speed of 1 mm/min, using a universal testing machine (Autograph AG-I, 100 kN, manufactured by Shimadzu Corporation) to measure the flexural strength and flexural modulus. The mean values are presented in the tables (N=5).

Shear Adhesion Test Against Enamel

The labial surfaces of bovine mandibular incisors were ground with #80 silicon carbide paper (manufactured by Nihon Kenshi Co., Ltd.) under running water to obtain samples with an exposed flat dentin surface. The sample tooth was secured to the tape stuck to the bottom of a mold having 15 holes (15-hole mold, manufactured by Ultradent Products Inc.; 35 mm in diameter×25 mm in height). Thereafter, a plaster was filled into the mold, and was cured by being allowed to stand for about 30 minutes. The sample was then removed from the mold, and ground with #600 silicon carbide paper (manufactured by Nihon Kenshi Co., Ltd.) under running water to a size large enough (at least 2.38 mm in diameter) to provide a bonding surface. The bonding surface was ultrasonically washed with water for 5 minutes.

Separately, a CR filling mold (Bonding Mold Insert, manufactured by Ultradent Products Inc.; Ø=2.38 mm) was installed in a dedicated instrument (Bonding Clamp, manufactured by Ultradent Products Inc.). The CR filling mold on the dedicated instrument was then lowered to make contact with the sample's bonding surface and fix the sample. Thereafter, the dental composite resin prepared in each Example and Comparative Example was filled into the holes of the CR filling mold to form a thin layer at most 1 mm thick. After adding another portion into the mold (filling about ⅔ of the mold, or about 2 mm thickness), the dental composite resin was left to stand for 10 seconds, and light was applied for 10 seconds with a dental LED photoirradiator (VALO manufactured by Ultradent Products Inc. under this trade name) to cure the self-adhesive dental composite resin. After cure, the sample was removed from the mold, and was used as an adhesion test sample. The adhesion test sample was immersed in distilled water, and was left to stand in distilled water for 24 hours inside a thermostatic chamber set at 37° C. The sample was then taken out of the chamber, and its bond strength was measured. For the measurement of bond strength (shear bond strength), the adhesion test sample was fitted to a dedicated holder (Test Base Clamp, manufactured by Ultradent Products Inc.), and the bond strength was measured by using a dedicated jig (Crosshead Assembly, manufactured by Ultradent Products Inc.) with a universal testing machine (manufactured by Shimadzu Corporation) at a crosshead speed of 1 mm/min. The mean values are presented in the tables (N=10).

TABLE 1

| Components (parts by mass) | | Example 1 | Example 2 | Example 3 | Example 4 | Example 5 | Example 6 | Example 7 | Example 8 |
|---|---|---|---|---|---|---|---|---|---|
| (Meth)acrylic compound (A) | UN-7700 | 10 | 5 | 15 | 20 | — | — | 10 | 10 |
| | UN-353 | — | — | — | — | 10 | — | — | — |
| | UN-350 | — | — | — | — | — | 10 | — | — |
| (Meth)acrylic compound | UN-2600 | — | — | — | — | — | — | — | — |
| | EBECRYL 8807 | — | — | — | — | — | — | — | — |
| Monomer (B) having an acidic group and a molecular weight of less than 5,000 | MDP | 10 | 10 | 10 | 10 | 10 | 10 | 10 | 10 |
| Monomer (C) having no acidic group and having a molecular | D-2.6E | 50 | 55 | 45 | 40 | 50 | 50 | 50 | 50 |
| | DD | 20 | 20 | 20 | 20 | 20 | 20 | 20 | 20 |

TABLE 1-continued

| Components (parts by mass) | | Example 1 | Example 2 | Example 3 | Example 4 | Example 5 | Example 6 | Example 7 | Example 8 |
|---|---|---|---|---|---|---|---|---|---|
| weight of less than 5,000 | MAEA | 10 | 10 | 10 | 10 | 10 | 10 | 10 | 10 |
| Polymerization initiator (D) | CQ | 0.2 | 0.2 | 0.2 | 0.2 | 0.2 | 0.2 | 0.2 | 0.3 |
| | Li-TPO | 1 | 1 | 1 | 1 | 1 | 1 | 1 | — |
| Polymerization accelerator (E) | DABE | 0.2 | 0.2 | 0.2 | 0.2 | 0.2 | 0.2 | 0.2 | 0.4 |
| Other | BHT | 0.05 | 0.05 | 0.05 | 0.05 | 0.05 | 0.05 | 0.05 | 0.05 |
| Filler (F) | Inorganic filler 1 | 10 | 10 | 10 | 10 | 10 | 10 | 10 | 10 |
| | Inorganic filler 2 | 170 | 170 | 170 | 170 | 170 | 170 | — | 170 |
| | Inorganic filler 3 | — | — | — | — | — | — | 170 | — |
| Polymerization shrinkage stress | MPa | 8.6 | 8.8 | 8.3 | 7.9 | 8.9 | 9.3 | 8.1 | 8.5 |
| Flexural modulus | GPa | 6 | 6.2 | 5.4 | 4.9 | 6.2 | 6.3 | 6.3 | 5.8 |
| Flexural strength | MPa | 95 | 101 | 92 | 86 | 103 | 104 | 100 | 90 |
| Shear bond strength to enamel | MPa | 10 | 9 | 10 | 8 | 9 | 8 | 10 | 8 |

TABLE 2

| Components (parts by mass) | | Comparative Example 1 | Comparative Example 2 | Comparative Example 3 | Comparative Example 4 |
|---|---|---|---|---|---|
| (Meth)acrylic compound (A) | UN-7700 | — | 10 | — | — |
| | UN-353 | — | — | — | — |
| | UN-350 | — | — | — | — |
| (Meth)acrylic compound | UN-2600 | — | — | 10 | — |
| | EBECRYL 8807 | — | — | — | 10 |
| Monomer (B) having an acidic group and a molecular weight of less than 5,000 | MDP | 10 | 0 | 10 | 10 |
| Monomer (C) having no acidic group and having a molecular weight of less than 5,000 | D-2.6E | 60 | 60 | 50 | 50 |
| | DD | 20 | 20 | 20 | 20 |
| | MAEA | 10 | 10 | 10 | 10 |
| Polymerization initiator (D) | CQ | 0.2 | 0.2 | 0.2 | 0.2 |
| | Li-TPO | 1 | 1 | 1 | 1 |
| Polymerization accelerator (E) | DABE | 0.2 | 0.2 | 0.2 | 0.2 |
| Other | BHT | 0.05 | 0.05 | 0.05 | 0.05 |
| Filler (F) | Inorganic filler 1 | 10 | 10 | 10 | 10 |
| | Inorganic filler 2 | 170 | 170 | 170 | 170 |
| | Inorganic filler 3 | — | — | — | — |
| Polymerization shrinkage stress | MPa | 10.5 | 8.1 | 10.8 | 11.3 |
| Flexural modulus | GPa | 6.6 | 5.9 | 6.4 | 6.9 |
| Flexural strength | MPa | 110 | 96 | 108 | 118 |
| Shear bond strength to enamel | MPa | 7 | 1 | 5 | 4 |

As shown in Table 1, the cured products of the self-adhesive dental composite resins according to the present invention (Examples 1 to 8) had a flexural strength of 80 MPa or higher, and a low polymerization shrinkage stress of less than 10 MPa. The cured products of these self-adhesive dental composite resins also showed a shear bond strength to enamel of 8 MPa or higher in the shear adhesion test simulating a situation with relatively deep cavities. These results suggested that containing the (meth)acrylic compound (A) reduces the polymerization shrinkage stress, and effectively reduces the risk of detachment and marginal leakage in restorative treatment of relatively deep cavities. In contrast, the dental composite resins that did not contain the (meth)acrylic compound (A) of the present invention (Comparative Examples 1, 3, and 4) had a polymerization shrinkage stress of 10 MPa or higher, confirming that a sufficient reduction of polymerization shrinkage stress was not achieved (Table 2). It was also confirmed that the shear bond strength to enamel was 7 MPa or less, as shown in Table 2. The dental composite resin that did not contain the monomer (B) having an acidic group (Comparative Example 2) had a shear bond strength to enamel of 1 MPa.

INDUSTRIAL APPLICABILITY

A dental composition according to the present invention can be suitably used as a self-adhesive dental composite resin, a dental bonding material, or a dental cement in the field of dentistry.

The invention claimed is:

1. A dental composition comprising: a (meth)acrylic compound (A) having a weight-average molecular weight of 5,000 to 50,000; a monomer (B) having an acidic group and a molecular weight of less than 5,000; a monomer (C) having no acidic group and having a molecular weight of less than 5,000; and a polymerization initiator (D), the (meth)acrylic compound (A) having a weight-average molecular weight of 1,250 or more and less than 20,000 per (meth)acryl group, wherein the polymerization initiator (D) comprises: a water-soluble photopolymerization initiator (D-1) having a solubility at 25° C. of 10 g/L or more in water; and a water-insoluble photopolymerization initiator (D-2) having a solubility at 25° C. of less than 10 g/L in water.

2. The dental composition according to claim 1, wherein the (meth)acrylic compound (A) is a urethanized (meth) acrylic compound (A-1).

3. The dental composition according to claim 2, wherein the urethanized (meth)acrylic compound (A-1) is a (meth) acrylate having: a structure selected from the group consisting of a polyester, a polycarbonate, a polyurethane, a polyether, a poly-conjugated diene, and a hydrogenated poly-conjugated diene; and a urethane bond.

4. The dental composition according to claim 1, wherein the content of the (meth)acrylic compound (A) is 0.1 to 30 parts by mass in total 100 parts by mass of the (meth)acrylic compound (A), the monomer (B) having an acidic group, and the monomer (C) having no acidic group.

5. The dental composition according to claim 1, wherein the (meth)acrylic compound (A) has a viscosity at 25° C. of 5,000 cps or more.

6. The dental composition according to claim 1, wherein the (meth)acrylic compound (A) has a glass transition temperature (Tg) of 20° C. or less.

7. The dental composition according to claim 1, wherein the (meth)acrylic compound (A) has a weight-average molecular weight of 6,100 or more and less than 20,000 per (meth)acryl group.

8. The dental composition according to claim 1, wherein the monomer (B) having an acidic group and a molecular weight of less than 5,000 comprises a phosphoric acid group-containing monomer.

9. The dental composition according to claim 1, wherein the monomer (C) having no acidic group and having a molecular weight of less than 5,000 comprises a hydrophobic monomer (C-1) having no acidic group and having a molecular weight of less than 5,000.

10. The dental composition according to claim 9, wherein the hydrophobic monomer (C-1) having no acidic group and having a molecular weight of less than 5,000 comprises an aliphatic compound-based bifunctional monomer.

11. A self-adhesive dental composite resin comprising a dental composition of claim 1.

12. A dental bonding material comprising a dental composition of claim 1.

13. A dental cement comprising a dental composition of claim 1.

14. The dental composition according to claim 1, wherein the (meth)acrylic compound (A) has a weight-average molecular weight of 12,100 to 50,000.

15. The dental composition according to claim 1, wherein the (meth)acrylic compound (A) has a weight-average molecular weight of 12,500 to 30,000.

16. The dental composition according to claim 1, wherein the (meth)acrylic compound (A) has a weight-average molecular weight of 12,500 to 20,000.

* * * * *